United States Patent [19]

Slinkard et al.

[11] 4,129,592

[45] Dec. 12, 1978

[54] HYDROCARBON OXIDATION PROCESS

[75] Inventors: William E. Slinkard; Anthony B. Baylis, both of Corpus Christi, Tex.

[73] Assignee: Celanese Corporation, New York, N.Y.

[21] Appl. No.: 674,357

[22] Filed: Apr. 7, 1976

[51] Int. Cl.² .............................................. C07C 51/20
[52] U.S. Cl. ..................................... 562/549; 252/452; 252/453; 252/456; 252/458; 252/467; 252/469; 260/604 R
[58] Field of Search ..................................... 260/533 R

[56] References Cited

U.S. PATENT DOCUMENTS

| | | | |
|---|---|---|---|
| 3,702,868 | 11/1972 | Santangelo et al. | 260/533 R |
| 3,907,833 | 9/1975 | Slinhard et al. | 260/533 R |

*Primary Examiner*—Vivian Garner
*Attorney, Agent, or Firm*—Linn I. Grim

[57] ABSTRACT

A vapor phase process is provided for high conversion of $C_4$-hydrocarbons to acetic acid in the presence of a catalyst comprising a calcined coprecipitate of a molybdenum compound and one or more compounds of metal elements selected from titanium, zirconium, tin, hafnium, niobium and tantalum.

8 Claims, No Drawings

HYDROCARBON OXIDATION PROCESS

BACKGROUND OF THE INVENTION

Processes for the oxidation of organic compounds such as hydrocarbons in the presence or absence of catalysts are well known. There is continuing applied research activity devoted to achieving economically feasible oxidation processes for commercial scale operation.

Numerous oxidation catalysts have been reported in the prior art, such as are disclosed in U.S. Pat. Nos. 2,904,580; 3,142,697; 3,179,694; 3,197,419; 3,198,750; 3,200,081; 3,200,084; 3,226,421; 3,248,340; 3,264,225; 3,251,900; 3,257,474; 3,260,768; 3,668,245; 3,702,868; 3,703,550; 3,856,824; 3,859,358; and the like.

Acetic acid is generally produced by the carbonylation of methanol or by the oxidation of acetaldehyde or hydrocarbons.

U.S. Pat. No. 3,282,994 describes a method for the oxidation of butane in liquid phase. U.S. Pat. No. 3,607,925 provides a process for the production of acetic acid by oxidation of butene-2 with nitric acid in the presence of a vanadium catalyst. U.S. Pat. No. 3,644,512 discloses a process for converting butane to acetic acid in liquid phase in the presence of a soluble cobalt compound.

Processes for the oxidation of hydrocarbons in the vapor phase by means of oxygen-containing gases have not proven entirely satisfactory primarily due to the excessive formation of undesirable carbon oxides, and to the difficulty in maintaining control of the highly exothermic oxidation reaction. U.S. Pat. No. 3,395,159 provides an improved process wherein the oxidation of hydrocarbons is performed in a reactor system having fused vanadium oxide catalyst coated on the inner surface of the reactor, which system has the advantage of better control and isothermal operation.

It is also known that it is possible to oxidize catalytically in vapor phase lower olefins into acetic acid and a high proportion of carbon oxides.

In practice the commercial processes for oxidation of hydrocarbons are difficult to manage, and inevitably the yield of desired product is low in comparison to the yield of carbon oxides and other oxidation by-products.

Accordingly, it is an object of the present invention to provide a commercially feasible process for oxidation of hydrocarbons.

It is another object of this invention to provide a vapor phase process for converting $C_4$-hydrocarbons into acetic acid.

It is another object of this invention to provide a process for oxidizing butane to acetic acid with high conversion efficiency and with a low yield of organic by-products.

Other objects and advantages shall become apparent from the following description and examples.

DESCRIPTION OF THE INVENTION

One or more objects of the present invention are accomplished by the provision of a process which comprises contacting $C_4$-hydrocarbon and oxygen in vapor phase with a reduced molybdenum catalyst, wherein said molybdenum catalyst is prepared by reducing a calcined mixture of molybdenum compound coprecipitated with one or more compounds of metal elements selected from the group consisting of titanium, zirconium, tin, hafnium, niobium and tantalum.

By the term "reduced molybdenum catalyst" is meant a metal oxide catalyst in which the molybdenum ions substantially are in a valence state of less than 6 preferably in the range of 4 to 5.5 (e.g., $MoO_2$) when introduced into the reaction system.

By the term "coprecipitated" is meant the precipitation from aqueous solution of soluble molybdenum compound and soluble compound(s) of the other active catalyst elements. The term also includes catalyst compositions which are precipitated from an aqueous medium in which one active catalyst element is slurried (e.g., $MoO_3$) and the other active catalyst element is dissolved (e.g., $TiCl_4$).

A convenient form of water soluble molybdenum compound is the commercially available ammonium heptamolybdate. In a preferred embodiment, the catalyst composition is prepared by coprecipitating from solution calculated proportions of soluble molybdenum compound and soluble compound(s) of titanium, zirconium, tin, hafnium, niobium and tantalum. A particularly effective soluble form of these active catalyst elements is the oxalate. Other useful derivative forms are halides, hydroxides, lactates, tartrates, citrates, acetylacetonates, and the like. In some cases of catalyst preparation, the addition of one active catalyst element solution to a second active catalyst element solution yields an immediate coprecipitation of catalyst elements. In other cases where coprecipitation is not spontaneous upon the blending of active catalyst element solutions, the coprecipitation is achieved by reducing the volume of aqueous medium.

The catalyst coprecipitate is recovered, dried and transformed into a powder having a particle size range between about 10 and 200 microns. The catalyst composition can also be prepared in the form of granules, pellets, and the like.

Another preferred method of preparing the invention catalyst is to coprecipitate the molybdenum and other active catalyst elements from solution onto a chemically inactive carrier such as $\alpha$-alumina, silica, titanium oxide, chromia, diatomaceous earth, carborundum, silica-alumina, boria, or other convenient support.

When preparing a supported molybdenum catalyst composition, the molybdenum content, calculated as the free metal, ranges between about 1 and 30 weight percent, based on the total weight of the supported catalyst. Instead of impregnating a gel of aluminum oxide and/or silicon oxide with the active catalyst elements, a mixed gel can be prepared by coprecipitation of all the oxides from a solution containing the corresponding soluble compounds.

In the invention molybdenum catalyst compositions the atomic ratio of molybdenum to other active catalyst elements in the composition can vary in the range between about 12:1 and 1:2, and preferably in the range between about 10:1 and 1:1.

After a molybdenum catalyst composition is recovered in the form of a coprecipitation as described hereinabove, it is subjected to a calcination procedure to convert all of the active catalyst elements into the form of the corresponding oxides. The catalyst calcination is conducted in an air or nitrogen stream at a temperature between about 300° C. and 650° C. for a period of time between about 4 and 20 hours. A preferred calcination temperature is in the range between about 400° C. and 600° C.

As a final step in the preparation of the invention molybdenum catalysts, the oxide composition which is recovered from the calcination treatment is converted into a higher state of catalytic activity by subjecting the said calcined composition to a reducing environment for a period of time between about 4 and 48 hours at a temperature in the range between about 300° C. and 600° C. This reducing treatment is conveniently accomplished by flowing a reducing gas such as ammonia, sulfur dioxide, hydrogen, carbon monoxide, hydrocarbons, and the like, in contact with the calcined molybdenum catalyst composition.

Catalyst can be reduced external to reactor or reduced in situ using feed gas of butane and oxygen or other reducing gases previously listed.

In the present invention process for catalytically reacting $C_4$-hydrocarbons with oxygen to produce acetic acid selectively in high yield, a hydrocarbon stream containing components selected from normal and iso butanes and butenes is mixed with oxygen gas and contacted in vapor phase with the reduced molybdenum catalyst composition provided as an embodiment of the present invention. The optimum temperature for the reaction varies between about 180° C. and 350° C., and generally in the range between about 225° C. and 300° C. The reduced molybdenum catalyst can be maintained in either a fixed bed or a fluid bed.

The contact time between the $C_4$-hydrocarbons and the reduced molybdenum oxide catalyst varies between about 0.5 and 15 seconds. A shorter contact time is advantageous if the process is to involve recycling of product stream effluent.

It is advantageous in the practice of the invention process to maintain the quantity of oxygen gas in the feed stream at a level which is the least required to convert efficiently the $C_4$-hydrocarbon stream to acetic acid. The quantity of oxygen gas in the feed stream usually is maintained in the range between about 0.03 and 5.0 moles per mole of $C_4$-hydrocarbons, and preferably in the range between about 0.05 and 3.0 moles.

In a preferred embodiment of the invention process, water is included in the feed stream in a quantity between about 0.1 and 2.0 moles per mole of $C_4$-hydrocarbons. The presence of water vapor in the oxidation reaction system increases the yield of acetic acid and lowers the yield of carbon oxides and maleic acid.

The recovery of the product stream and the separation of the acetic acid from acetaldehyde, maleic acid and other by-products can be accomplished by conventional procedures. U.S. Pat. No. 3,624,148 describes a method for the separation of acetic acid from maleic acid.

The following examples are further illustrative of the present invention. The reactants and other specific ingredients are presented as being typical, and various modifications can be devised in view of the foregoing disclosure within the scope of the invention.

EXAMPLE A

Preparation of Catalysts

Calcination of the various materials was achieved at the temperature stated in a large stagnant air muffler furnace without temperature programming. Hydrogen reduction was conducted in a tube furnace. The material was placed in the center of a 2-inch diameter Pyrex or Vycor tube, well flushed with $H_2$, heated rapidly to 200° C., then the temperature was programmed up to the final stated temperature over a period of 5 hours, held at that temperature for about 12 hours, and then rapidly cooled to room temperature still under the $H_2$ atmosphere.

1. $Mo_7SnO_x$ Catalyst $SnCl_4 \cdot 5H_2O$ (133g) dissolved in 100 ml of water was added dropwise with rapid stirring to $(NH_4)_6Mo_7O_{24} \cdot 4H_2O$ (494g) and $NH_4Cl$ (107g) dissolved in 1220 ml of water. A white precipitate formed immediately. The reaction mixture was heated to about 60° C. and stirred an additional 10 minutes after the addition was complete. The precipitate was collected by filtration, washed several times with water, and dried at 90° C. overnight. The dried solid was reduced with $H_2$ at 400° C.

2. $Mo_{10}SnO_x$ Catalyst $MoO_3$ (144g) and oxalic acid ($H_2C_2O_4 \cdot 2H_2O$ - 252g) were added to 600 ml of hot water and stirred until all of the reagents had dissolved. $SnC_2O_4$ (20.7g) was then added in small portions. The color of the reaction mixture changed immediately to brown and then to a dark green after all of the $SnC_2O_4$ had been added. The water was removed on a rotary evaporator and the recovered solid calcined at 500° C. for about 16 hours followed by hydrogen reduction at 400° C.

3. $Mo_4SnO_x$ Catalyst $SnCl_4 \cdot 5H_2O$ (131.5g) was dissolved in 300 ml of water and $NH_4Cl$ (37.1g) was added slowly and allowed to dissolve. The combined solution was filtered and the filtrate added dropwise to $(NH_4)_6Mo_7O_{24} \cdot 4H_2O$ (200g) dissolved in 400 ml of water. A precipitate formed immediately. After the addition was complete, the reaction mixture was warmed to about 60° C. and stirred for an additional hour. The precipitate was collected on a filter washed twice with hot water, dried at 90° C. and then calcined for about 16 hours at 500° C. and reduced with hydrogen at 400° C.

4. $Mo_7NbO_x$ Catalyst

Niobic acid (hydrated niobium oxide $Nb_2O_5 \cdot 7H_2O$, 39g) and oxalic acid ($H_2C_2O_4 \cdot 2H_2O$ 75.6g) were heated together in 500 ml of water overnight. Almost all of the solid material dissolved. The reaction mixture was added slowly to $(NH_4)_6Mo_7O_{24} \cdot 4H_2O$ (228.7g) dissolved in 500 ml of water with periodic addition of ammonium hydroxide to maintain the pH at about 7. A white precipitate formed immediately. The reaction mixture was placed on a rotary evaporator and the water removed. The resulting solid was dried at 90° C., calcined at 540° C. for about 16 hours and then reduced with hydrogen at 400° C.

5. $Mo_4TaO_x$ Catalyst $(NH_4)_6Mo_7O_{24} \cdot 4H_2O$ (247.2g) was dissolved in 500 ml of $H_2O$ and the $Ta(HC_2O_4)_5$ (13.8 wt. % Ta as a complex Ta oxalate) (463g) added slowly with stirring. A precipitate formed after about one half of the Ta had been added. After addition, the reaction mixture was stirred for 1 hour, placed on a rotary evaporator, the water removed, and the residue dried at 80° C. The dried solid was calcined at 500° C. for about 16 hours and reduced with hydrogen at 400° C.

6. $Mo_5TiO_x$ Catalyst $TiCl_4$ (59.8g) was weighed out in an inert atmosphere and dissolved in 200 ml of conc. HCl. The Ti solution was added dropwise with stirring to $(NH_4)_6Mo_7O_{24} \cdot 4H_2O$ (263.2g) dissolved in 600 ml of water. A precipitate formed immediately. The pH of the reaction mixture was adjusted to about 4 with $NH_4OH$. The precipitate was recovered by filtration, washed several times with water, and dried at 80° C. The dried solid was calcined at 500° C. for about 16 hours and reduced with H$_2$ at 400° C.

7. Mo$_7$ZrO$_x$ Catalyst

ZrCl$_4$ (46.4g) was dissolved in 200 ml of concentrated HCl and added dropwise with stirring to (NH$_4$)$_6$Mo$_7$O$_{24}$ · 4H$_2$O (247.2g) dissolved in 1 liter of hot water. A precipitate formed immediately. After addition was complete, the pH of the reaction mixture was adjusted to about 6 with NH$_4$OH and stirred an additional hour. The precipitate was collected on a filter, washed several times with H$_2$O, dried, and calcined at 500° C. for about 16 hours followed by hydrogen reduction at 400° C.

8. Mo$_7$HfO$_x$ Catalyst

HfCl$_4$ (25.0g) was added dropwise with stirring to 300 ml of H$_2$O while maintaining the pH of the reaction mixture at about 7 by simultaneously adding NH$_4$OH. The resulting precipitate was collected on a filter, washed several times with H$_2$O, then dissolved with H$_2$C$_2$O$_4$ · 2H$_2$O (37.8g) in 200 ml of hot H$_2$O. The Hf oxalate solution was then added dropwise to (NH$_4$)$_6$Mo$_7$O$_{24}$ · 4H$_2$O (96.4g) dissolved in 300 ml of hot H$_2$O and placed on a rotary evaporator and the water removed. The recovered solid was calcined at 500° C. for about 16 hours followed by hydrogen reduction at 400° C.

9. Mo$_{10}$Ti$_2$SnO$_x$ Catalyst

TiCl$_4$ (53.1g) and SnCl$_4$ · 5H O (49.1g) were dissolved in 200 ml of concentrated HCl and added dropwise with stirring to the (NH$_4$)$_6$Mo$_7$O$_{24}$ · 4H$_2$O (247.2 g) dissolved in 1 liter of hot H$_2$O. A precipitate formed immediately. After addition was complete, the pH of the reaction mixture was adjusted to about 6 with ammonium hydroxide and allowed to stir for an additional hour. The precipitate was collected on a filter, washed several times with H$_2$O, dried, calcined at 500° C. for about 16 hours and then reduced with hydrogen at 400° C.

10. Mo$_{14}$Sn$_2$NbO$_x$ Catalyst

SnCl$_4$ · 5H$_2$O (70.1g) and NbCl$_5$ (27.0g) were dissolved in 200 ml of concentrated HCl and added dropwise with stirring to the (NH$_4$)$_6$Mo$_7$O$_{24}$ · 4H$_2$O (247.2g) dissolved in 1 liter of hot H$_2$O. A precipitate formed immediately. The pH of the reaction mixture was maintained between 5 and 7 by simultaneously adding ammonium hydroxide. The precipitate was recovered by filtration, dried, calcined at 500° C. for about 16 hours and reduced with hydrogen at 400° C.

11. Mo$_{14}$Nb$_2$TiO$_x$ Catalyst

NbCl$_5$ (54.0g) and TiCl$_4$ (19.0g) were dissolved in 300 ml of concentrated HCl and added dropwise with stirring to the (NH$_4$)$_6$Mo$_7$O$_{24}$ · 4H$_2$O (247.2g) dissolved in one liter of hot H$_2$O. A precipitate formed immediately. After addition was complete, the pH of the reaction mixture was adjusted to about 6 with ammonium hydroxide and allowed to stir for an additional hour. The precipitate was collected on a filter, dried, calcined at 500° C. for about 16 hours, and reduced with hydrogen at 400° C.

Vapor Phase Oxidation Procedures

Standard screening conditions were a feed gas composition ratio of butane/oxygen/steam of 9/1/5 to 11/1/6 with a total flow rate of about 150 ml/min. A pressure of 5–10 psig was maintained in each reactor. The reactors consisted of U-shaped stainless steel tubes with the catalyst-containing section about 55 centimeters long with an inside diameter of about 1.0 centimeter. A 10 gram bed of 20/30 mesh catalyst was employed. Material balances were collected over periods of 5–16 hours, and entailed wet chemical analysis (gas chromatograph and titration of acid with base) of liquid products collected in an ice-cooled trap. Oxygen and carbon oxides in the vent were analyzed on a Fisher-Hamilton gas partitioner and gas samples of the vent were analyzed for acetaldehyde and butenes. Butane conversion was determined by difference.

EXAMPLE B

| | Production of Acetic Acid | | |
|---|---|---|---|
| Catalyst Preparation Reference | 1. | 2. | 3. |
| Catalyst | Mo$_7$SnO$_x$ | Mo$_{10}$SnO$_x$ | Mo$_4$SnO$_x$ |
| Reactor Temperature, °C. | 270 | 280 | 261 |
| Butane Conversion, % (1) | 2.3–2.4 | 2.4–2.6 | 2.5–2.6 |
| Oxygen Conversion, % (2) | 98–100 | 99 | 100 |
| Carbon Efficiency, % (3,4) | | | |
| Butenes | 4–5 | 1–4 | 2–3 |
| Acetic acid | 49–52 | 46–49 | 49–51 |
| Acetaldehyde | 0.4–1.1 | 3 | 0.6–0.8 |
| Maleic acid | 4 | 3–5 | 3–4 |
| Acrylic acid | 0.2 | 0.5–0.6 | 0.1–0.2 |
| Carbon monoxide | 13–16 | 14 | 13–14 |
| Carbon dioxide | 23–25 | 26–28 | 28–30 |
| Catalyst Preparation Reference | 4. | 5. | 6. |
| Catalyst | Mo$_7$NbO$_x$ | Mo$_4$TaO$_x$ | Mo$_5$TiO$_x$ |
| Reactor Temperature, °C. | 292 | 267 | 283 |
| Butane Conversion, % (1) | 2.3–2.4 | 2.3–2.4 | 2.0 |
| Oxygen Conversion, % (2) | 88–91 | 99 | 97–99 |
| Carbon Efficiency, % (3,4) | | | |
| Butenes | 2–3 | 6 | 6–8 |
| Acetic acid | 50–52 | 44–45 | 40–43 |
| Acetaldehyde | 2–3 | 0.1–0.2 | 0.4–0.5 |
| Maleic acid | 3–6 | 7 | 6–7 |
| Acrylic acid | 2 | 1 | 0.3–0.5 |
| Carbon monoxide | 13–16 | 11 | 16–21 |
| Carbon dioxide | 17–19 | 28–29 | 24–25 |
| Catalyst Preparation Reference | 7. | 8. | |
| Catalyst | Mo$_7$ZrO$_x$ | | Mo$_7$HfO$_x$ |
| Reactor Temperature, °C. | 297 | | 0.3 |
| Butane Conversion, % (1) | 1.7–1.8 | | 0.3 |
| Oxygen Conversion, % (2) | 67 | | 12 |
| Carbon Efficiency, % (3,4) | | | |
| Butenes | 13 | | 22 |

-continued

| Production of Acetic Acid | | | |
|---|---|---|---|
| Acetic acid | 40–41 | | 23 |
| Acetaldehyde | 2 | | 19 |
| Maleic acid | 7–8 | | 5 |
| Acrylic acid | 3 | | 1 |
| Carbon monoxide | 13 | | 9 |
| Carbon dioxide | 19 | | 16 |
| Catalyst preparation reference | 9. | 10. | 11. |
| Catalyst | $Mo_{10}Ti_2SnO_x$ | $Mo_{14}Sn_2NbO_x$ | $Mo_{14}Nb_2TiO_x$ |
| Reactor temperature, °C | 256 | 277 | 292 |
| Butane conversion, % | 2.5–2.6 | 2.2–2.4 | 2.1–2.3 |
| Oxygen conversion, % | 98–99 | 99 | 99 |
| Carbon Efficiency, % | | | |
| Butenes | 3 | 3 | 6 |
| Acetic acid | 45–47 | 42–43 | 42–44 |
| Acetaldehyde | 1 | 1–2 | 0.7 |
| Maleic acid | 3–6 | 3–5 | 4–6 |
| Acrylic acid | 0.1–0.3 | 0.3 | 1–2 |
| Carbon monoxide | 16–18 | 18 | 16–17 |
| Carbon dioxide | 25–30 | 31 | 27–28 |

FOOTNOTES (1) Butane conversion =
$$\frac{\text{moles of butane in} - \text{moles of butane out}}{\text{moles of butane in}} \times 100\%.$$

(2) Oxygen conversion =
$$\frac{\text{moles of oxygen in} - \text{moles of oxygen out}}{\text{moles of oxygen in}} \times 100\%$$

(3) Carbon efficiency was calculated on a carbon accounted for basis, e.g. acetic acid efficiency =
$$\frac{\text{g-atoms of carbon in acetic acid recovered}}{\text{g-atoms of carbon recovered in all products}} \times 100\%.$$

(4) Samples were also analyzed for acetone, formaldehyde, methyl ethylketone, 1-and 2-butanols, propionic, butyric, and formic acids. The concentration of these compounds was low (generally </Wt %) with no one product predominating.

What is claimed is:

1. A process for producing acetic acid which comprises contacting butane and an oxygen containing gas in the vapor phase with a reduced molybdenum catalyst, wherein said molybdenum catalyst is prepared by coprecipitating a molybdenum compound and one or more compounds of a metal selected from the group consisting of Ti, Zr, Sn, Hf, Nb and Ta from an aqueous solution or slurry; calcining the precipitate in air or nitrogen at about 300°–650° C. for about 4–20 hours; and reducing the calcined composition by contacting with a reducing gas at about 300°–600° C. for about 4–48 hours.

2. A process in accordance with claim 1 wherein the butane and an oxygen containing gas are contacted with the molybdenum catalyst in the presence of water vapor.

3. A process for producing acetic acid in accordance with claim 1 which comprises contacting butane, an oxygen containing gas and water in the vapor phase at a temperature between about 180° and 350° C.

4. A process in accordance with claim 3 wherein the oxygen containing gas is present in a quantity between about 0.05 and 3 moles per mole of butane.

5. A process in accordance with claim 3 wherein the water vapor is present in a quantity between about 0.1 and 2.0 moles per mole of butane.

6. A process in accordance with claim 3 wherein the atomic ratio of molybdenum to other metal elements in the catalyst is in the range between about 12:1 and 1:2.

7. A process in accordance with claim 3 wherein the catalyst is supported on a carrier.

8. A process in accordance with claim 3 wherein the contact time of butane with the catalyst is between about 0.5 and 15 seconds.

* * * * *